United States Patent [19]

Yeh et al.

[11] 4,203,923

[45] May 20, 1980

[54] METHOD FOR PROMOTION OF PHENOL HYDROGENATION

[75] Inventors: Chuen Y. Yeh, Succasunna; Harry E. Ulmer, Morris Township, Morris County, N.J.

[73] Assignee: Allied Chemical Corporation, Morris Township, Morris County, N.J.

[21] Appl. No.: 667,760

[22] Filed: Mar. 17, 1976

Related U.S. Application Data

[63] Continuation-in-part of Ser. No. 527,467, Nov. 26, 1974, abandoned.

[51] Int. Cl.$^2$ .................... C07C 41/00; C07C 46/15
[52] U.S. Cl. ............................................. 568/362
[58] Field of Search .................................. 260/586 P

[56] References Cited

U.S. PATENT DOCUMENTS

| | | | |
|---|---|---|---|
| 2,829,166 | 4/1958 | Jous et al. | 260/586 P |
| 3,076,810 | 2/1963 | Duggan et al. | 260/586 P |
| 3,187,050 | 6/1965 | Duggan et al. | 260/586 P |
| 3,305,586 | 2/1967 | Phelix | 260/586 P |
| 3,692,845 | 9/1972 | Cheema et al. | 568/754 |
| 3,959,382 | 5/1976 | Yeh et al. | 260/586 P |

FOREIGN PATENT DOCUMENTS 892562  2/1972  Canada ................................ 260/586 P Primary Examiner—Norman Morgenstern
Attorney, Agent, or Firm—J. B. Murray; A. M. Dorenberg

[57] ABSTRACT

A method for promoting the hydrogenation of phenol to cyclohexanone in the presence of a non-promoted palladium catalyst which comprises effecting the hydrogenation reaction in the presence of an in situ promoter selected from the group consisting of alkalie metal and alkaline earth metal chlorides, fluorides, bicarbonates, carbonates, hydroxides and nitrates, ammonia, ammonium hydroxide, secondary amines and mixtures thereof.

10 Claims, No Drawings

METHOD FOR PROMOTION OF PHENOL HYDROGENATION

CROSS-REFERENCE TO RELATED APPLICATION

This is a continuation-in-part of application Ser. No. 527,467 filed Nov. 26, 1974, now abandoned.

BACKGROUND OF THE INVENTION

1. FIELD OF THE INVENTION

This invention relates to the hydrogenation of phenol and more particularly to the promotion of the hydrogenation of phenol to cyclohexanone in the presence of a non-promoted palladium catalyst.

2. DESCRIPTION OF THE PRIOR ART

In the hydrogenation of phenol employing a palladium catalyst, the activity of the catalyst, and hence the rate of hydrogenation, decreases with continued use of the catalyst due to impurities present in the hydrogenation reaction mixture which poison the catalyst. While processes, such as those disclosed in in U.S. Pat. Nos. 3,692,845 and 3,187,050 have been developed to purify organic compounds such as phenol to be hydrogenated, poisoning of metallic catalysts has not been entirely eliminated in large scale commercial processes due to long-term accumulation of impurities, such as those impurities which are introduced with the starting material and the hydrogen gas, and those impurities which result from apparatus corrosion. In addition, by-products formed during the reduction cycle may have an adverse effect upon the metallic catalysts. Moreover, while the process of U.S. Pat. No. 3,692,845 effectively removes carbonyl-bearing impurities from phenol by treatment of the phenol with a polyamine, any polyamine remaining in the phenol fed to hydrogenation acts as a poison to the catalyst.

To avoid the economically prohibitive alternatives of discarding poisoned catalyst or continuing to use the poisoned catalyst at a reduced rate of hydrogenation, it is desirable to promote the rate of hydrogenation, thereby overcoming the disadvantages of continued use of such poisoned palladium catalysts. The hydrogenation of phenol to cyclohexanone has been promoted by the use of "promoted palladium-on-carbon catalysts", i.e. catalysts which have been treated, prior to their addition to the hydrogenation reaction mixture, to incorporate on the catalysts a material which enhances their activity. Thus, in U.S. Pat. No. 3,076,810, cyclohexanone is produced by the hydrogenation of phenol in the presence of a sodium-promoted catalyst, i.e. a palladium catalyst which has been chemically modified, prior to its introduction to the reaction mixture, to incorporate sodium thereon. While such catalysts effect an increase in the rate of hydrogenation, the use of promoted catalysts is disadvantageous due to the expense of time and process equipment needed to treat the catalyst to incorporate the selected material thereon prior to the addition of the promoted catalyst to the hydrogenation reaction mixture. Moreover, the addition to the hydrogenation reaction mixture of compounds such as the inorganic alkaline reacting compounds of U.S. Pat. No. 3,076,810 to further enhance the hydrogenation of phenol in the presence of a promoted palladium catalyst has not avoided the expensive and time consuming procedures necessary in the preparation of the promoted catalysts themselves.

SUMMARY OF THE INVENTION

In accordance with the present invention, promotion of hydrogenation of phenol to cyclohexanone in the presence of a non-promoted palladium catalyst is provided by a process which comprises effecting the hydrogenation reaction in the presence of an in situ promoter selected from the group consisting of alkali metal and alkaline earth metal chlorides, fluorides, bicarbonates, carbonates, hydroxides and nitrates, ammonia, ammonium hydroxide, secondary amines and mixtures thereof.

The process of the present invention has unexpectedly achieved promotion of phenol hydrogenation to cyclohexanone while employing a non-promoted palladium catalyst. By a "nonpromoted palladium catalyst" is meant a palladium catalyst which has not been chemically modified, prior to its addition to the hydrogenation reaction mixture, to incorporate in or on the catalyst materials which enhances its activity. As used herein, the term "chemically modified" does not include treatment of a metallic catalyst to cause the catalyst to be dispersed in, or absorbed on the surface of, an inert support. Nor does the term "chemically modified" include treatment of a catalyst to alter either the amount or ionic character of metallic catalyst present therein. Furthermore, "chemically modified" does not include treatment of the palladium catalyst to incorporate therein, or to admix therewith, additional catalytically active metals, i.e. the transition elements.

By use of a non-promoted catalyst, the present invention avoids the expense in both time and equipment which results from the preparation of promoted palladium catalysts. The improved rates of hydrogenation achieved by the process of the present invention are especially significant in view of the large tonnages of palladium catalysts used annually by industry in the hydrogenation of phenol to cyclohexanone. Furthermore, the in situ promoters of the present invention have been unexpectedly found to promote the hydrogenation of phenol to cyclohexanone without appreciably increasing the amount of cyclohexanol produced by the further hydrogenation of the desired cyclohexanone hydrogenation product. Thus, recovery of cyclohexanone from the hydrogenation product system, as by distillation, is not further complicated by the formation of additional undesired products, i.e. cyclohexanol.

The ability of the in situ promoters of the present invention, e.g. the chlorides, fluorides, bicarbonates, carbonates, hydroxides and nitrates of alkali and alkaline earth metals, to promote phenol hydrogenation to cyclohexanone is particularly surprising in view of the prior art teaching (U.S. Pat. No. 2,829,166) of the undesirability of the presence of compounds such as sodium hydroxide in phenol hydrogenation mixtures employing non-promoted catalysts. Moreover, while U.S. Pat. No. 2,891,096 teaches that organic amines, and especially tertiary amines of the aliphatic or cyclic type, are effective as in situ promoters for the hydrogenation of phenol to cyclohexanol, applicants have discovered that only secondary amines are in situ promoters for the hydrogenation of phenol to cyclohexanone in the presence of a non-promoted palladium catalyst, and that the presence in such a hydrogenation reaction mixture of other amines, such as the tertiary amines preferred by U.S. Pat. No. 2,891,096, impede rather than promote the desired hydrogenation of phenol to cyclohexanone.

Finally, it has been surprisingly found that the in situ promoters of the present invention prevents poisoning of non-promoted palladium catalysts in hydrogenation media containing residual polyamines, e.g. those polyamine additives employed in U.S. Pat. No. 3,692,845 to pre-treat phenol for removal of carbonyl-bearing impurities, which may carry over into the hydrogenation media.

DETAILED DESCRIPTION OF THE INVENTION

According to the present invention, promotion of the hydrogenation of phenol to cyclohexanone in the presence of a non-promoted palladium catalyst is provided by effecting the hydrogenation reaction in the presence of an in situ promoter selected from the group consisting of alkaline metal and alkaline earth metal, chlorides, fluorides, bicarbonates, carbonates, hydroxides and nitrates, ammonia, ammonium hydroxide, secondary amines and mixtures thereof.

The palladium catalysts useful in the present invention may contain palladium in either its elemental or combined form as catalytically active metal. The palladium is generally absorbed on the surface of an inert support. Such supports are well known and include for example, active carbon, silica, alumina, diatomaceous earth, kieselguhr and mixtures thereof. Exemplary of supported palladium catalysts which may be employed in the present invention are palladium oxide, palladium-on-carbon and palladium black, palladium-on-carbon being preferred. While the amount of palladium incorporated on the selected inert support may vary widely, when the selected metallic hydrogenation catalyst is a palladium-on-carbon catalyst, the catalyst contains from about 0.1 to 50 weight percent palladium, and most preferably from about 0.2 to 10 weight percent. A satisfactory and commercially available catalyst contains 5 weight percent palladium-on-charcoal. In addition, the palladium catalysts useful in the present invention may contain catalytically active metals in addition to palladium. Such additional catalytically active metals which may be employed are those selected from the group consisting of elements of the platinum series. Exemplary of platinum metal series which may be employed are ruthenium, rhodium, osmium, iridium, platinum and mixtures thereof.

The phenol which may be employed in the present invention may be obtained from conventional sources, such as by the oxidation of cumene to form cumene hydroperoxide and the decomposition of the resulting hydroperoxide. The phenol preferably contains not greater than about 20 ppm, and most preferably not greater than 10 ppm, sulfur values (calculated as elemental sulfur); preferably not greater than 2 ppm, and most preferably not greater than 1 ppm, iron values (calculated as elemental iron); and preferably not greater than 100 ppm, and most preferably not greater than 50 ppm, acetol (i.e., hydroxy-2-propanone). As used herein, the term "sulfur values" refers to sulfur in either its elemental or combined form. Exemplary of combined forms of sulfur are compounds containing sulfate, sulfide and sulfite groups, sulfonic acids and mercaptans.

The process of the present invention may be employed to promote phenol hydrogenation for non-promoted palladium catalysts which have been poisoned by wide variety of S/Fe-free impurities, i.e. impurities other than those which contain sulfur or iron in either its elemental or combined form. The concentration in the phenol of S/Fe-free impurities may vary widely, but is generally from about 50 to 4000 ppm and preferably from about 100 to 1000 ppm S/Fe-free impurities. However, phenol having a higher or lower level of S/Fe-free impurities may also be employed. S/Fe-free impurities capable of poisoning or inactivating palladium catalysts which can be promoted by the present invention typically include deleterious nitrogen compounds, i.e. nitrogen-containing compounds which inhibit the hydrogenation of phenol to cyclohexanone employing such non-promoted palladium catalysts. Deleterious nitrogen compounds which are conventionally present in phenol hydrogenation mixtures include: ammonium salts, e.g. $NH_4Cl$, $(NH_4)_3PO_4$ and $NH_4I$; hydroxylamine salts, e.g. hydroxylamine hydrochloride; urea; tertiary amines, e.g. triethylamine and tributylamine; primary amines, e.g. n-hexylamine and n-butylamine; and polyamines, e.g. the polyamines employed in U.S. Pat. No. 3,692,845 to treat phenol to remove carbonyl-bearing impurities. Typical polyamines include hexamethylene diamine and hexamethylene tetraamine. Of course, the effect which a given impurity has upon a palladium catalyst varies widely according to the character of the palladium incorporated on the carbon support (i.e. the relative amounts of elemental palladium and ionic palladium employed thereon), the conditions of temperature and pressure employed during hydrogenation, the concentration of the impurity and catalyst in the hydrogenation reaction mixture and other factors.

While not required, the phenol hydrogenated in accordance with the process of the present invention may be first treated to remove at least a portion of impurities therein, for example, by use of one or more purification processes such as those disclosed in U.S. Pat. Nos. 3,187,050 and/or 3,692,845. Thus, the phenol hydrogenated using the process of the present invention may be first conditioned as in U.S. Pat. No. 3,187,050 by admixing the phenol with a conditioning agent selected from the group consisting of ethylenediaminetetraacetic acid (i.e. EDTA) and alkali metal salts thereof, heating the resulting mixture at a temperature of at least 80° C. for at least one hour and distilling off the conditioned phenol, thereby removing at least a portion of the metallic-impurities, sulfur-containing, and halogen-containing impurities, alpha-methylstyrene and acetophenone. Alternatively, the phenol may be first purified by contacting the phenol with a polyamine disclosed in U.S. Pat. No. 3,692,845 and recovering the treated phenol by distillation, to remove at least a portion of carbonyl-bearing impurities.

The in situ promoters of the present invention are members selected from the group consisting of alkali and alkaline earth metal chlorides, fluorides, bicarbonates, carbonates, hydroxides and nitrates, ammonia, ammonium hydroxide, secondary amines, and mixtures thereof. Secondary amines preferred in the present invention are members selected from the group consisting of compounds having the formula R N(R")H, wherein R and R" are the same or different and are alkyl having 1 to 20 carbon atoms, and most preferably from 2 to 10 carbon atoms. Examples of secondary amines wherein R and R" are as defined above are diisopropylamine, diethylamino, methyl butylamine, 2-(N-methylamino)-heptane, di-n-octadecylamine, (n-hexadecyl)propylamine and dioctylamine. Exemplary of alkali metal and alkaline earth metal salts which may be employed as in situ promoters are sodium hydroxide, sodium carbonate, potassium chloride, magnesium fluoride, calcium bicarbonate and sodium nitrate. Preferred as promoters in the present invention are alkali metal and alkaline earth metal bicarbonates, carbonates and nitrates, ammonium hydroxide and secondary amines. Especially preferred promoters are $NaNO_3$, $Na_2CO_3$, $BaNO_3$, $Ba_2CO_3$, $CaNO_3$, $Ca_2CO_3$, diisopropylamine and mixtures thereof. The selected promoter may be added to the hydrogenation reaction mixture as a phenol slurry containing up to about 25 weight percent, and preferably from about 1 to 10 weight percent, of the selected promoter. Alternatively, the promoter may be added to the hydrogenation reaction mixture directly or, in the case of gaseous ammonia, it may be sparged to the reaction mixture.

The amount of promoter added to the hydrogenation reaction mixture may also vary widely, and is generally not greater than about 3 percent by weight of the hydrogenation reaction mixture, and preferably from about 0.01 to 1 percent by weight. When deleterious nitrogen impurities, such as ammonium salts, polyamines, urea, and tertiary and primary amines, are present in the hydrogenation reaction mixture, an in situ promoter selected from the group consisting of alkali metal chlorides, bicarbonates, carbonates and nitrates is preferably added to the hydrogenation reaction mixture in an amount of from about 1 to 6 ppm promoter (calculated as the alkali metal) per ppm deleterious nitrogen (calculated as elemental nitrogen), and preferably 2 to 4 ppm promoter per ppm deleterious nitrogen, present in the reaction mixture.

The selected promoter may be introduced to the hydrogenation reaction mixture either prior to hydrogenation or during hydrogenation. Thus, the conditions of temperature and pressure under which the promoter may be added to the hydrogenation mixture are not critical and may vary widely. For example, the temperature at which the promoter is added to the hydrogenation reaction mixture may vary from about 25° to about 260° C. and the pressure may vary from about atmospheric to 200 psig. While an improved rate of hydrogenation is generally observed immediately upon addition to the hydrogenation reaction mixture of a promoter of the present invention, even more improved results may be obtained where the hydrogenation reaction mixture is maintained at a temperature within the range of about 170° to 185° C. and a pressure of from about 60 to 80 psig. for a period of 15 to 30 minutes after addition thereto of the selected promoter after which period the hydrogenation mixture is returned to the conditions of hydrogenation and the hydrogenation reaction is allowed to continue.

The selected in situ promoter may be added to the hydrogenation reaction mixture and the reaction product may be withdrawn from the hydrogenation vessel either continuously or batchwise. Upon withdrawal of the hydrogenation product from the reaction vessel, the palladium catalyst may be recovered from the product stream and returned to the vessel for hydrogenation of additional phenol. The recovery of the catalyst from the product stream may be effected by any standard solids separation procedure, e.g. centrifugation, vacuum filtering and the like.

The in situ promoters of the present invention may be removed from the product stream in a similar manner since the in situ promoters of the present invention are substantially insoluble in both the product stream and the phenol hydrogenation mixture. Uon reclamation from the reaction product of the promoters employed during hydrogenation, the separated in situ promoter may be returned to the hydrogenation of additional phenol.

Vessels which may be employed during the hydrogenation are conventional and include the typical hydrogenation apparatus, such as for example, Magne Drive Autoclave.

The process of the present invention is further illustrated by reference to the following examples, wherein parts are by weight unless otherwise indicated.

In the following examples, each phenol which is to be hydrogenated is obtained first by admixing 200 parts of commercial grade phenol produced by the thermal decomposition of cumene hydroperoxide with 0.08 part of Sequestrene NA3T (manufactured by Ciba-Geigy, having the formula

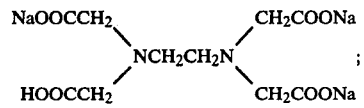

0.37 part hexamethylenetriamine (HMTA) and 0.08 part sodium hydroxide. The mixture is heated at a temperature of about 150° C. and at atmospheric pressure. with continuous stirring for a period of about 2 hours. After this period, the heated mixture is distilled until a residue comprising about 10% of the original mixture remains, thereby recovering as overhead treated phenol which comprises about 90% of the distilled mixture (i.e., about 180 parts phenol). The phenol so recovered is substantially free of the Sequestrene, NA3T, HMTA and NaOH additives. From the 180 parts phenol, 160 parts are withdrawn and used for hydrogenation, as described in the following examples.

The commercial grade phenol which is treated as above and the phenol after treatment are found to have contain the following impurities:

| Impurity | Impurity Concentration (ppm) in: Commercial Grade Phenol | Treated Phenol |
|---|---|---|
| acetone | 47 | 31 |
| mesityl oxide | 199 | 4 |
| cumene | 54 | 6 |
| acetol | 1728 | (n.d.)* |
| alpha-methyl styrene | 1791 | 295 |
| methyl benzofuran | 104 | 34 |
| acetophenone | 1395 | 105 |
| dimethylphenyl carbinol | 1 | 10 |
| unknowns | 485 | 178 |
| Total | 5804 | 663 |

*none detected

EXAMPLE 1

A mixture of 160 parts of phenol treated as above and containing 0.2 part of fresh, non-promoted 5 percent palladium-on-carbon catalyst is introduced into a stainless steel Magne Drive autoclave. Gaseous hydrogen is introduced into the reactor and the mixture is hydrogenated at a temperature of 185° C. and a pressure of 70 psig. Samples of the hydrogenation reaction mixture are taken at periodic intervals and analyzed to determine the cyclohexanone content thereof. The results of this standard run are summarized in Table I below.

In six separate runs (Runs 1-6), the above hydrogenation procedure is repeated employing phenol containing 0.2 part of fresh, non-promoted palladium-on-carbon catalyst in addition to an in situ promoter of the present invention, in the amounts shown in Table I. The improved rates of hydrogenation, expressed as percent promotion, obtained by the use of the in situ promoters are summarized in Table I.

mixture for each run are taken at periodic intervals and analyzed for their cyclohexanone content and the results obtained are summarized in Table II below. The improved rates of hydrogenation (expressed as percent promotion relative to the standardization run of Example 1) achieved by the use of the in situ promoters are also summarized in Table II.

TABLE II

| Run No. | In Situ Promoter | Promoter ppm | HMDA ppm | 'One and 'Ol Content* of Hydrogenation Mixture At (min.): | | | | | | | Percent** Promotion |
|---|---|---|---|---|---|---|---|---|---|---|---|
| | | | | | 30 | 60 | 90 | 120 | 150 | 175 | |
| 7 | Na₂CO₃ | 385 | 258 | 'one | 32.2 | 48.0 | 57.6 | 65.5 | — | 76.8 | 103 |
| | | | | 'ol | — | — | — | — | — | 0.9 | |
| 8 | Na₂CO₃ | 400 | 120 | 'one | 37.7 | 56.5 | 68.6 | — | 80.9 | — | 122 |
| | | | | 'ol | — | — | 1.4 | — | 4.0 | — | |
| 9 | Na₂CO₃ | 392 | 378 | 'one | 39.7 | 50.5 | 57.8 | — | 68.5 | — | 109 |
| | | | | 'ol | — | 0.3 | 0.7 | — | 2.7 | — | |
| 10 | NaNO₃ | 630 | 400 | 'one | 35.8 | 51.0 | 57.2 | — | 67.3 | — | 110 |
| | | | | 'ol | 0.6 | — | 1.3 | — | 3.6 | — | |

*'one = cyclohexanone; 'ol = cyclohexanol. Content expressed as weight percent.
**Based on cyclohexanone content at 60 min.

TABLE I

| Run No. | In Situ Promoter | Promoter ppm | 'One and 'Ol Content* of Hydrogenation Mixture At (min): | | | | | | | Percent Promotion** |
|---|---|---|---|---|---|---|---|---|---|---|
| | | | | 30 | 45 | 60 | 75 | 90 | 150 | |
| Standard | — | — | 'one | 29.9 | — | 46.5 | — | 57.8 | 69.2 | 100 |
| | | | 'ol | — | — | 0.7 | — | 0.9 | 1.7 | |
| 1 | NH₄OH | 245 | 'one | 43.5 | — | 67.3 | — | 97.0 | — | 145 |
| | | | 'ol | — | — | — | — | — | — | |
| 2 | Gaseous NH₃ | 65 | 'one | 36.7 | — | 65.6 | — | 80.8 | — | 141 |
| | | | 'ol | — | — | — | — | — | — | |
| 3 | BaCl₂ | 69 | 'one | 47.3 | — | 59.2 | — | 71.5 | 85.7 | 127 |
| | | | 'ol | — | — | — | — | 1.9 | 4.7 | |
| 4 | CaCl₂ | 33 | 'one | 36.9 | — | 51.0 | — | 64.8 | 71.2 | 110 |
| | | | 'ol | — | — | 1.1 | — | 2.2 | 4.5 | |
| 5 | Diisopropylamine | 92 | 'one | 44.0 | — | 71.6 | — | 90.6 | 97.5 | 154 |
| | | | 'ol | — | — | 0.6 | — | 1.2 | 2.5 | |
| 6 | Na₂CO₃ | 410 | 'one | 59.0 | 72.8 | 89.2 | 91.8 | — | — | 192 |
| | | | 'ol | — | 1.3 | 2.4 | 6.9 | — | — | |

*'one = cyclohexanone; 'ol = cyclohexanol. Content expressed as weight percent.
**Based on cyclohexanone content at 60 min.

EXAMPLE 2

In separate runs, selected amounts of hexamethylenediamine (HMDA) and 160 parts phenol are admixed with 0.25 part of fresh, non-promoted 5 percent palladium-on-carbon catalyst in a Magne Drive autoclave at a temperature of 180° C. and a pressure of 70 psig. for a period of 2 and one-half hours. At the end of the above period the catalyst, poisoned with the above deleterious nitrogen compound, is first isolated by vacuum filtration and then passed to a second Magne Drive autoclave for hydrogenation of a substantially pure phenol portion. No catalyst activity for phenol reduction to cyclohexanone is found for the poisoned catalyst. The poisoned catalyst is then recovered and 0.2 parts of poisoned catalyst is admixed with 160 parts of phenol containing the selected amount of an in situ promoter of the present invention. Each mixture is then individually hydrogenated under the above temperature and pressure conditions. Samples of the hydrogenation reaction

EXAMPLE 3

To determine the effect which primary and tertiary amines have upon hydrogenation of phenol in the presence of non-promoted palladium catalysts, a mixture of 160 parts of phenol containing 0.2 part of fresh, non-promoted 5 percent palladium-on-carbon catalyst is introduced into a stainless steel Magne Drive autoclave and the phenol hydrogenated as in the standard run of Example 1, i.e. at a temperature of 185° C. and a pressure of 70 psig. The results of this standard run are summarized in Table III below. In four separate runs (Runs 11-14), the above hydrogenation procedure is repeated employing phenol containing 0.2 part of fresh, non-promoted palladium-on-carbon catalyst in addition to the amine indicated in Table III. The rates of hydrogenation, expressed as percent promotion, obtained in each run are summarized in Table III. as shown, the primary and tertiary amines in Runs 11-13 do not effect the increased rates of hydrogenation which are obtained in Run 14 employing a secondary amine.

TABLE III

| Run No. | Amine | Amine ppm | 'One and 'Ol Content* of Hydrogenation Mixture At (min.): | | | | | Percent** Promotion |
|---|---|---|---|---|---|---|---|---|
| | | | | 30 | 60 | 90 | 150 | |
| Standard | None | — | 'one | 32.4 | 50.6 | 61.0 | 68.9 | 100 |
| | | | 'ol | — | — | 0.8 | 2.0 | |
| 11 | n-hexylamine | 100 | 'one | 33.6 | 50.5 | 58.4 | 68.0 | 96 |

TABLE III-continued

| Run No. | Amine | Amine ppm | | 'One and 'Ol Content* of Hydrogenation Mixture At (min.): | | | | Percent** Promotion |
|---|---|---|---|---|---|---|---|---|
| | | | | 30 | 60 | 90 | 150 | |
| 12 | triethylamine | 105 | 'ol | — | 0.6 | 1.1 | 1.5 | 76 |
| | | | 'one | — | 40.2 | 46.3 | 56.7 | |
| 13 | 2,2-dimethoxy-ethylamine | 135 | 'ol | — | — | — | 0.5 | 62 |
| | | | 'one | 27.5 | 34.5 | 37.8 | 39.7 | |
| 14 | diisopropylamine | 92 | 'ol | — | — | — | 0.5 | 157 |
| | | | 'one | 47.7 | 77.9 | 95.6 | 97.1 | |
| | | | 'ol | — | 0.6 | 1.2 | 2.5 | |

* 'one = cyclohexanone; 'ol = cyclohexanol. Content expressed as weight percent.
**Based on cyclohexanone content at 90 min.

EXAMPLE 4

To determine the effect which sodium hydroxide has upon hydrogenation of phenol in the presence of non-promoted palladium catalysts, a mixture of 160 parts of phenol (pH 5.2) containing 0.2 part of fresh, non-promoted 5 percent palladium-on-carbon catalyst is introduced into a stainless steel Magne Drive autoclave and the phenol hydrogenated at a temperature of from about 186° to 188° C. and a pressure of 70 psig. The results of this standard run are summarized in Table IV below. In a separate run, the above hydrogenation procedure (hydrogenation temperature=187° to 188° C.) is repeated employing phenol containing 0.2 part of fresh, non-promoted palladium-on-carbon catalyst in addition to 0.4 part of an aqueous solution containing 50 weight percent sodium hydroxide, resulting in a phenol mixture having a pH of 6.52. The rates of hydrogenation, expressed as percent promotion, obtained in this run is summarized in Table IV. As shown, the sodium hydroxide provides promotion of cyclohexanone hydrogenation as compared to the standard run up to a hydrogenation time of about 75 minutes, after which the cyclohexanol content of the hydrogenation mixture increases at the expense of the cyclohexanol yield.

TABLE IV

| Run No. | In Situ Promoter | Promoter ppm | | 'One and 'Ol Content* of Hydrogenation Mixture At (Min.): | | | | | | | | |
|---|---|---|---|---|---|---|---|---|---|---|---|---|
| | | | | 30 | 45 | 60 | 75 | 90 | 105 | 120 | 135 | 165 |
| Standard | None | — | 'one | 37.9 | 55.0 | 68.8 | 78.7 | 86.6 | 92.3 | 95.0 | 95.5 | 94.6 |
| | | | 'ol | 0.3 | 0.6 | 0.8 | 1.2 | 1.4 | 2.2 | 2.8 | 3.3 | 4.3 |
| 15 | NaOH | — | 'one | 46.8 | 66.1 | 82.3 | 87.2 | 85.2 | 75.0 | 68.6 | 63.0 | — |
| | | | 'ol | 0.1 | 0.5 | 1.2 | 1.4 | 5.8 | 5.3 | 14.7 | 17.5 | — |

* 'One = cyclohexanone; 'Ol = cyclohexanol. Content expressed as weight percent

While there have been described various embodiments of the invention, the methods described are not intended to be understood as limiting the scope of the invention as it is realized that changes therewithin are possible and it is further intended that each element recited in any of the following claims is to be understood as referring to all equivalent elements for accomplishing substantially the same results in substantially the same or equivalent manner, it being intended to cover the invention broadly in whatever form its principle may be utilized.

We claim:

1. In a process for producing cyclohexanone by the hydrogenation of phenol in the presence of a nonpromoted palladium catalyst, the improvement which comprises adding to the hydrogenation reaction mixture a promoter selected from the group consisting of ammonia, ammonium hydroxide, secondary amines and mixtures thereof.

2. The process according to claim 1 wherein said palladium catalyst is a supported catalyst.

3. The process according to claim 2 wherein said palladium catalyst is palladium-on-carbon catalyst.

4. The process according to claim 1 wherein said phenol contains deleterious nitrogen impurities.

5. The process according to claim 5 wherein said deleterious nitrogen impurities are present in the phenol in an amount of from about 50 to 4000 ppm.

6. The process according to claim 1 wherein said promoter is a secondary amine selected from the group consisting of amines corresponding to the formula R'N(R")H wherein R' and R" are the same or different and are alkyl from 1 to 20 carbon atoms.

7. The process according to claim 1 wherein said promoter is ammonia or ammonium hydroxide.

8. The process according to claim 1 wherein the phenol contains not greater than about 20 ppm sulfur values (calculated as elemental sulfur), not greater than 2 ppm iron values (calculated as elemental sulfur), and not greater than 100 ppm acetol.

9. The process according to claim 1 wherein up to 3 weight percent promoter is added by weight of phenol.

10. The process according to claim 1 wherein between about 0.01 and 1 weight percent promoter is added by weight of phenol.

* * * * *

UNITED STATES PATENT AND TRADEMARK OFFICE
CERTIFICATE OF CORRECTION

PATENT NO. : 4,203,923

DATED : May 20, 1980

INVENTOR(S) : Chuen Y. Yeh and Harry E. Ulmer

It is certified that error appears in the above-identified patent and that said Letters Patent are hereby corrected as shown below:

Column 10, line 31, claim 5, "5" should read --4--.

Signed and Sealed this

Nineteenth Day of August 1980

[SEAL]

Attest:

SIDNEY A. DIAMOND

Attesting Officer

Commissioner of Patents and Trademarks